(12) United States Patent
Barbera et al.

(10) Patent No.: US 12,310,942 B2
(45) Date of Patent: May 27, 2025

(54) PHARMACEUTICAL COMPOSITIONS COMPRISING STATINS AND HYALURONIC ACID DERIVATIVES

(71) Applicant: FIDIA FARMACEUTICI S.p.A., Abano Terme (IT)

(72) Inventors: Carlo Barbera, Abano Terme (IT); Andrea Pastorello, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 847 days.

(21) Appl. No.: 17/604,142

(22) PCT Filed: Apr. 15, 2020

(86) PCT No.: PCT/IB2020/053530
§ 371 (c)(1),
(2) Date: Oct. 15, 2021

(87) PCT Pub. No.: WO2020/212853
PCT Pub. Date: Oct. 22, 2020

(65) Prior Publication Data
US 2022/0193032 A1 Jun. 23, 2022

(30) Foreign Application Priority Data
Apr. 18, 2019 (IT) .................. 102019000006038

(51) Int. Cl.
*A61K 31/366* (2006.01)
*A61K 31/728* (2006.01)
*A61K 45/06* (2006.01)
*A61K 47/36* (2006.01)

(52) U.S. Cl.
CPC .......... *A61K 31/366* (2013.01); *A61K 31/728* (2013.01); *A61K 45/06* (2013.01); *A61K 47/36* (2013.01)

(58) Field of Classification Search
CPC ..... A61K 31/366; A61K 31/728; A61K 45/06
See application file for complete search history.

(56) References Cited

U.S. PATENT DOCUMENTS

| 2018/0169136 A1 | 6/2018 | Ho et al. |
| 2020/0230288 A1 | 7/2020 | Cho et al. |

FOREIGN PATENT DOCUMENTS

| EP | 1 853 279 B1 | 5/2013 |
| WO | WO 02/36096 A2 | 5/2002 |
| WO | WO 2016/201682 A1 | 12/2016 |
| WO | WO 2017/039294 A1 | 3/2017 |
| WO | WO 2018/143736 A1 | 8/2018 |

OTHER PUBLICATIONS

Bae et al., "Photo-cured hyaluronic acid-based hydrogels containing simvastatin as a bone tissue regeneration scaffold", Biomaterials, 2011, vol. 32, pp. 8161-8171.
International Search Report, issued in PCT/IB2020/053530, dated Jul. 8, 2020.
Written Opinion of the International Searching Authority, issued in PCT/IB2020/053530, dated Jul. 8, 2020.

*Primary Examiner* — Kamal A Saeed
(74) *Attorney, Agent, or Firm* — Birch, Stewart, Kolasch & Birch, LLP

(57) ABSTRACT

The present invention relates to pharmaceutical compositions comprising mixtures of a statin and a hyaluronic acid amide derivative which are useful in the treatment of inflammation and degradation of osteoarthritic joint cartilage, in particular post-traumatic osteoarthrosis and osteoarthrosis caused by physiological joint aging, and in the treatment of other joint disorders such as rheumatoid arthritis.

2 Claims, 3 Drawing Sheets

PHARMACEUTICAL COMPOSITIONS COMPRISING STATINS AND HYALURONIC ACID DERIVATIVES

The present invention relates to pharmaceutical compositions comprising mixtures of a statin and a hyaluronic acid amide derivative which are useful in the treatment of inflammation and degradation of osteoarthritic joint cartilage, in particular post-traumatic osteoarthrosis and osteoarthrosis caused by physiological joint aging, and in the treatment of other joint disorders such as rheumatoid arthritis.

PRIOR ART

Osteoarthrosis is the most common form of arthritis, and is one of the major unmet clinical needs among musculoskeletal disorders. Although it is traditionally considered to be a "wear and tear" disorder that leads to cartilage destruction, OA is currently viewed as a complex disorder involving inflammatory components released by cartilage, synovial fluid and bone.

The use of statins as a potential treatment for osteoarthritis has been clinically reported in observational studies (Kadam 2013; Clockaerts 2012) conducted on patients who underwent cholesterol control treatment with this class of drugs. The efficacy of statins in reducing the main inflammatory effects observed in osteoarthrosis and rheumatoid arthritis, both in vitro and in vivo, is also reported in the literature. See, in particular, Dombrecht 2007 and Yudoh 2010 for simvastatin, Simopopulou 2009 and Pathak 2014 for atorvastatin, and Baker 2012 for pravastatin.

However, the benefits deriving from oral use of said statins are limited by the need to use high therapeutic doses to obtain therapeutic effects in the joint.

Moreover, the bioavailability of statins is limited by their bond with the plasma proteins and hepatic metabolism; various in vitro studies have demonstrated that the efficacy of statins in preclinical models of osteoarthrosis is obtained at concentrations in the micromolar range, whereas the plasma concentration of statins in patients treated orally is in the nanomolar range (Dulak et al., 2005). For example, the plasma levels of atorvastatin in patients to whom doses of 10-80 mg/day per os are prescribed range from 2 to 200 nmol/litre, whereas the anti-inflammatory effect of statins seems to be achieved at micromolar concentrations. This raises the problem of reaching the effective dose to be administered in order to obtain a therapeutic benefit in osteoarthrosis patients without substantially increasing the risk of side effects, including headaches, muscle pains, hyperglycaemia and increased risk of diabetes.

Some attempts have been made to administer the statin directly by the intra-articular route, either alone (Dinc 2012, Akasaki 2009) or combined with other ingredients, in order to improve its efficacy, stability and characteristics in general. For example, EP 2446884 combines statins with linear hyaluronic acid to increase the well-known anti-inflammatory properties of the latter and improve its performance, especially in the treatment of rheumatoid arthritis; Goto 2017 tested the efficacy of a single administration of fluvastatin, loaded into PLGA microbeads, in an animal model.

DESCRIPTION OF THE INVENTION

It has now surprisingly been found that the anti-inflammatory and chondroprotective effects typical of statins can be synergically amplified, compared with statins alone and with the combination with linear hyaluronic acid (HA), by combining statins with hyaluronic acid amide derivatives.

The object of the invention is therefore pharmaceutical compositions comprising a statin and a hyaluronic acid amide derivative; the compositions, in gel form, can be administered locally or locoregionally directly into the joint cavity, the periarticular area and/or the periosseous area.

The HA amide derivatives used according to the invention, known from EP1095064 and EP1853279, are selected from hexadecyl, octadecyl and dodecyl amides, more preferably the hexadecyl amide prepared from an HA with a weight average molecular weight ranging from 500 kDa to 730 kDa, and having an average degree of amidation ranging from 0.1% to 10% molar, preferably from 1% to 3% molar, detected by HPLC after hydrolysis of the amide and conjugation of the hexadecylamine released with a fluorophoric substance. The hexadecyl amide having the characteristics stated above and an average degree of derivatisation ranging from 1% to 3% molar is described in EP1853279, and is available under the name of HYADD®-4.

"Average molecular weight" here means the weight-average molecular weight, calculated by the "intrinsic viscosity" method (Terbojevich et al., *Carbohydr Res*, 1986, 363-377).

The statins that can be used are preferably simvastatin, mevastatin, pravastatin, lovastatin, atorvastatin, fluvastatin and rosuvastatin. The preferred statins are atorvastatin, simvastatin and fluvastatin.

The compositions according to the invention can be prepared by suspending the statin in an aqueous solution buffered at a pH close to neutral, such as PBS. The HA amide derivative is added to the resulting suspension. The resulting gel is then filtered and sterilised by conventional techniques, for example in the autoclave.

When the amide derivative is HYADD®-4, its concentration ranges from 5 to 15 mg/mL, and is preferably 8 mg/mL. The concentration of the statin ranges from 0.1 to 15 mg/mL, preferably from 0.5 to 10 mg/mL.

The mixture is sterilised in the autoclave when the statin used is thermostable; in the case of statins that are not thermostable (such as simvastatin), various methods can be used. For example, the hydrogel of HYADD®-4 can be mixed under sterile conditions with powdered active ingredient pre-sterilised with gamma rays; as an alternative to powder, the active ingredient can take the form of a tablet or small freeze-dried cake, always prepared from the sterilised powder. Alternatively, a kit can be made up with a double syringe, one containing HYADD®-4 hydrogel sterilised in the autoclave and the other containing powdered active ingredient sterilised with gamma rays. In this case, the contents of the two syringes are mixed homogeneously at the time of use.

The compositions according to the invention constitute a controlled-release system by gradually releasing the statin over time as a result of hydrophobic interactions with the hydrocarbon chain of the hyaluronic acid amide derivative.

Local and/or locoregional, and in particular intra-articular, administration increases efficacy at the target site, allowing the use of very low doses of active ingredients and thus eliminating the common problems deriving from systemic administration (poor distribution in the target anatomical area) and the onset of adverse effects associated with the high dose.

The composition is also wholly biocompatible and bioresorbable, as it consists of an HA derivative already used in the viscosupplementation treatment of osteoarthrosis and has a long residence time, since the HA amide forms compact hydrogels, unlike linear HA.

The synergy of the combination between an HA amide derivative, in particular HYADD®-4, and a statin was demonstrated by measuring the release of collagen and MMP-13 from bovine cartilage explant cultures. The results are shown in the examples and figures below.

The compositions therefore protect the joint cartilage against inflammatory damage, which may be induced by trauma, progressive aging of the joint structure or disease, and can be successfully used in the local and/or locoregional, in particular intra-articular, treatment of osteoarthrosis in general, and post-traumatic osteoarthrosis, osteoarthrosis caused by physiological joint aging and rheumatoid arthritis in particular.

Figure 1:
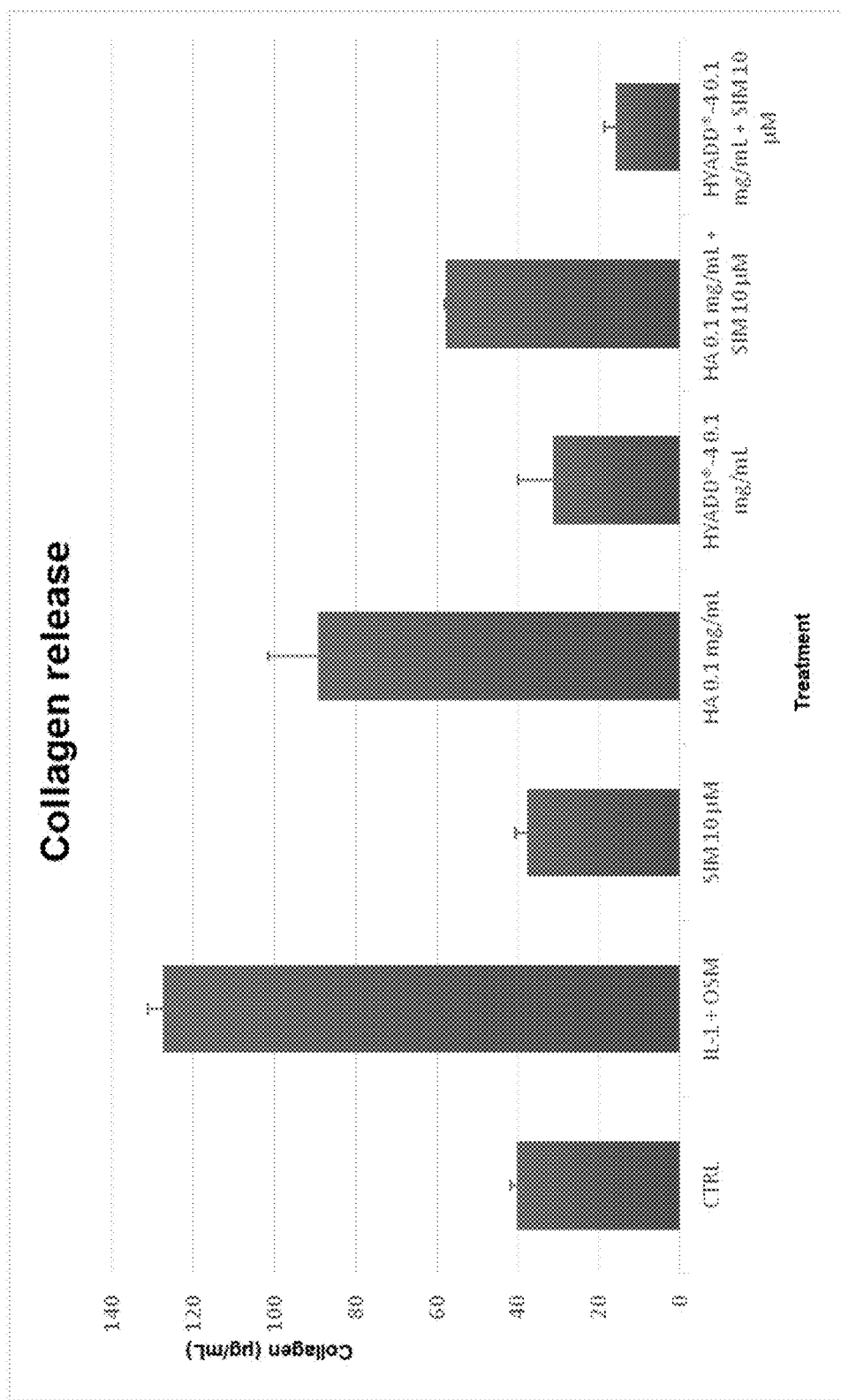
FIG. 1: effect of simvastatin (SIM), either alone or combined with linear hyaluronic acid (HA) or HYADD®-4, in reducing collagen release.

The invention is illustrated in detail in the examples below.

Example 1: Preparation of a Gel Consisting of HYADD®-4 (8 mg/mL) and Atorvastatin (5 mg/mL)

30 mL of 10 mM PBS, pH 7.4±0.1, is poured into a 200 mL reactor equipped with a stirrer; 0.5 g of atorvastatin is then added and the mixture is maintained under stirring for 1 hour to allow uniform dispersion of the powder in the solution; 70 ml of PBS pH 7.4±0.1 is added and, while maintaining stirring, 0.8 g of HYADD®-4 is added; the mixture is left under stirring for 3 hours, and then left to stand for at least 3 hours. The resulting gelled suspension (100 mL) is mixed for 30 minutes, filtered through a stainless steel filter with a porosity of 105 μm, and mixed again for at least 10 minutes. The suspension is then introduced into syringes and sterilised in the autoclave.

Example 2: Preparation of a Gel Consisting of HYADD®-4 (8 mg/mL) and Atorvastatin (1 mg/mL)

30 mL of 10 mM PBS, pH 7.4±0.1, is poured into a 200 mL reactor equipped with a stirrer; 0.1 g of atorvastatin is then added and the mixture is maintained under stirring for 1 hour to allow uniform dispersion of the powder in the solution; 70 ml of PBS pH 7.4±0.1 is added and, while maintaining stirring, 0.8 g of HYADD®-4 is added; the mixture is left under stirring for 3 hours, and then left to stand for at least 3 hours. The resulting gelled suspension (100 mL) is mixed for 30 minutes, filtered through a stainless steel filter with a porosity of 105 μm, and mixed again for at least 10 minutes. The suspension is then introduced into syringes and sterilised in the autoclave.

Example 3: Preparation of a Gel Consisting of HYADD®-4 (8 mg/mL) and Simvastatin (5 mg/mL) with Mixing of the Presterilised Ingredients 100 ml of 4 mM PBS, pH 7.0±0.1, is poured into a 200 mL reactor equipped with a stirrer; 0.8 g of HYADD®-4 is poured into the reactor, under stirring; stirring is maintained for about an hour, and the mixture is then left to stand for at least 3 hours. The resulting gel (100 mL) is mixed for at least 10 minutes, filtered through a stainless steel filter with a porosity of 105 μm, and mixed again for at least a further 10 minutes. The gel is then sterilised in the autoclave.

100 mL of gel containing 8 mg/mL of HYADD®-4, obtained and sterilised as described above, is poured, under laminar-flow hood (in aseptic conditions), into a 200 mL reactor equipped with a stirrer and sterilised; 0.5 g of simvastatin powder sterilised with gamma rays is then added, and the mixture is maintained under stirring for 3 hours to allow uniform dispersion of the powder in the gel. The resulting sterile suspension is then introduced into syringes.

Example 4: Preparation of a Gel Consisting of HYADD®-4 (8 mg/mL) and Simvastatin (5 mg/mL) in a Kit with a Double Syringe 100 ml of 4 mM PBS, pH 7.0±0.1, is poured into a 200 mL reactor equipped with a stirrer; 0.8 g of HYADD®-4 is added to the reactor, under stirring; stirring is maintained for about an hour, and the mixture is then left to stand for at least 3 hours. The resulting gel (100 mL) is mixed for at least 10 minutes, filtered through a stainless steel filter with a porosity of 105 μm, and mixed again for at least a further 10 minutes.

At this point the gel is aliquoted into 5 mL syringes at the quantity of 3 ml of gel per syringe, and the syringes (type A) are sterilised in the autoclave.

15 mg of simvastatin powder is introduced into 5 mL syringes, and the syringes thus filled (type B) are sterilised by gamma irradiation.

The type A syringe is connected to the type B syringe at the time of use with a luer-lok (female-female) connector. The contents of syringe A are decanted into syringe B and then from B to A. This operation is repeated 4 times, to obtain a sterile suspension of simvastatin homogeneously dispersed in the HYADD®-4-based gel.

Example 5: Preparation of a Gel Consisting of HYADD®-4 (8 mg/mL) and Atorvastatin (5 mg/mL) in a Kit with a Double Syringe 100 ml of 4 mM PBS, pH 7.0±0.1, is poured into a 200 mL reactor equipped with a stirrer; 0.8 g of HYADD®-4 is added to the reactor, under stirring; stirring is maintained for about an hour, and the mixture is then left to stand for at least 3 hours. The resulting gel (100 mL) is mixed for at least 10 minutes, filtered through a stainless steel filter with a porosity of 105 μm, and mixed again for at least a further 10 minutes.

At this point the gel is aliquoted into 5 mL syringes at the quantity of 3 ml of gel per syringe, and the syringes (type A) are sterilised in the autoclave.

15 mg of atorvastatin powder is introduced into 5 mL syringes, and the syringes thus filled (type B) are sterilised by gamma irradiation.

The type A syringe is connected to the type B syringe at the time of use with a luer-lok (female-female) connector. The contents of syringe A are decanted into syringe B and then from B to A. This operation is repeated 4 times, to obtain a sterile suspension of atorvastatin homogeneously dispersed in the HYADD®-4-based gel.

Example 6: Ex Vivo Cartilage Degradation Test

The efficacy of the conjugate was evaluated with an ex vivo cartilage inflammation model described in Chang 2014. Cartilage was harvested from the patello-femoral sulcus and from adult bovine femoral condyles, and cartilage biopsies (Ø=3 mm) were taken with a steel punch. The biopsies were cultured in a 48-well Multiwell plate (B D Falcon, cat. no. 353078, Italy) at 37° C. 5% $CO_2$ for 24 hours in DMEM/F-12 (1:1) (Life Technologies, cat. no. 11320074, Italy) containing 2% foetal bovine serum (Life Technologies, cat. no. 10270106, Italy). After incubation, the biopsies were washed with PBS 1× (Euroclone, cat. no. ECB4004L) and divided into groups:
1) a control group, wherein the biopsies were neither treated nor stimulated;
2) one group exposed to OSM and IL-1β pro-inflammatory cytokines (10 ng/mL each);
3) one group exposed to OSM and IL-1β and treated with HYADD®-4 (0.1 mg/mL);
4) one group exposed to OSM and IL-1β and treated with 700 kDa linear HA (0.1 mg/mL);
5) one group exposed to OSM and IL-1β and treated with simvastatin (10 μM);
6) one group exposed to OSM and IL-1β and treated with 700 kDa linear HA combined with simvastatin 10 μM;
7) one group exposed to OSM and IL-1β and treated with HYADD®-4 combined with simvastatin 10 μM.

After 7, 14 and 21 days, the biopsy culture medium was aspirated and replaced with fresh culture medium containing the inflammatory cytokines and the compounds under study. After 21 days of incubation, the biopsy medium is collected and the soluble collagen released is measured with the Sircol collagen assay kit (Biocolor, cat. no. S1000, UK) according to the manufacturer's instructions. As will be seen in FIG. 1, the biopsies of the group treated with OSM and IL-1β release a significantly higher amount of soluble collagen into the culture medium than the control. Simvastatin alone is able to significantly reduce collagen release from biopsies treated with an inflammatory stimulus. Linear HA also exhibits a reduction effect on collagen release into the medium, which is far more marked in the cells treated with HYADD®-4 alone. Combined use of HA and simvastatin significantly inhibits collagen release compared to the positive control (IL-1/OSM), but not substantially differently from the effect of simvastatin alone. Conversely, combined use of HYADD®-4 and simvastatin shows a surprising effect of marked reduction of collagen release from the treated biopsies; said value is significantly greater than that of simvastatin and HYADD®-4 used alone at the same concentrations.

Example 7: MMP-13 Expression Evaluation Test

Figure 2:
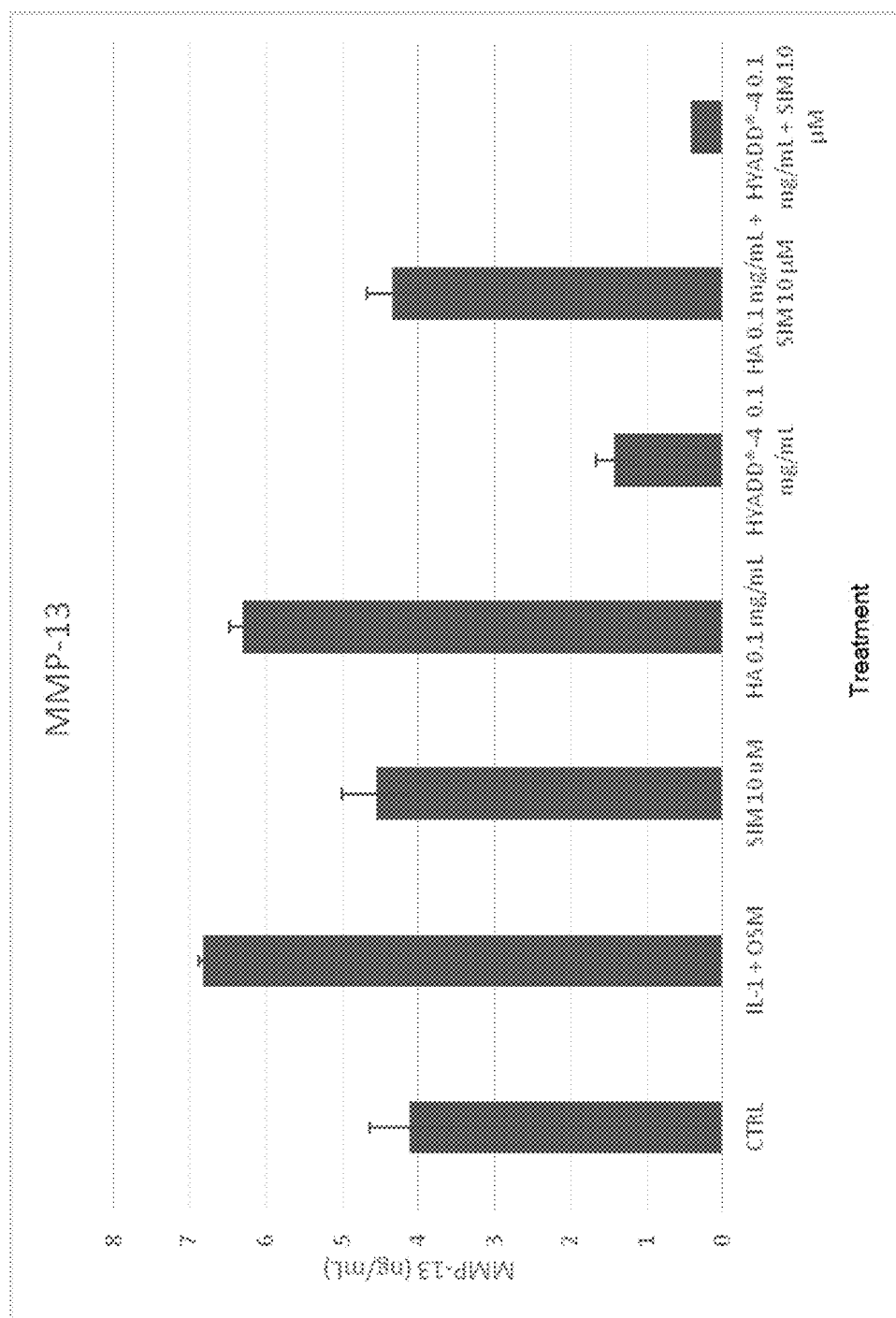
FIG. 2: effect of simvastatin (SIM), either alone or combined with linear hyaluronic acid (HA) or HYADD®-4, in reducing MMP-13 production.

The MMP-13 concentration in the supernatants obtained from the collagen release efficacy tests described above was determined with an ELISA assay (Mybiosource, cat. no. MBS2880297, USA) used according to the kit manufacturer's instructions, to quantify the presence in the samples of the enzyme mainly responsible for cartilage degradation. The results set out in FIG. 2 demonstrate, as expected, that treatment of samples with the inflammatory cytokines OSM and IL-1β significantly increases the MMP-13 concentration in the supernatant. Simvastatin alone cancels out the effect induced by the inflammatory stimulus, restoring the MMP-13 concentrations to values equal to those measured in the control (CTRL). HA alone does not significantly reduce MMP-13 release compared with the control; conversely, HYADD®-4 significantly inhibits MMP-13 release into the biopsy culture medium. As regards the mixtures, MMP-13 concentrations not significantly different from those obtained with simvastatin alone were observed in the supernatants of the biopsies treated with the HA 0.1 mg/mL-simvastatin mixture.

Conversely, the HYADD®-4-simvastatin mixture proved exceptionally effective in reducing MMP-13 production, reducing the values to much lower levels than those observed for Hymovis alone.

This confirms that the HYADD®-4-simvastatin mixture exerts a synergic effect on reducing the production of MMP-13, which is the metalloprotease mainly responsible for cartilage breakdown.

Example 8: Comparison of Efficacy Between Statins

The efficacy of simvastatin, atorvastatin and lovastatin in reducing the inflammatory effects induced by exposure of bovine cartilage biopsies to cytokines IL-1β and OSM was evaluated. For this purpose, cartilage biopsies were collected from the patello-femoral sulcus and femoral condyles from the femur of 1 adult bovine (15-18 months). The biopsy sites showed no signs of degradation or swelling on visual inspection. The biopsies (Ø=3 mm) were taken with a steel punch.

Each biopsy was transferred to a well of a 48-well MW and washed twice with 500 μL PBS 1× (Euroclone, cat. no. ECB4004L, Italy). 500 μL DMEM/F-12 (Life Technologies, cat. no. 11320074, Italy)+2% FBS (Life Technologies, cat. no. 10270106, Italy) were then added to the wells. The biopsies were incubated for 24 h at 37° C. 5% $CO_2$. After incubation, the biopsies were washed with 500 μL PBS 1×, and 500 μL DMEM/F-12+2% FBS containing the dilution of the compound to be tested were added to all the wells. Each statin was used at the concentrations of 10 μM and 2.5 μM. 4 biopsies were used for each condition. After 7, 14 and 21 days, the biopsy culture medium was aspirated and replaced with 500 μL of fresh culture medium containing the appropriate concentrations of pro-inflammatory cytokines (IL-1β and OSM, 10 ng/mL) and the active ingredients to be tested. The biopsy culture medium was harvested after 21 days and used to determine the soluble collagen content. The Sircol assay was conducted according to the manufacturer's instructions, and quantitation was effected by spectrophotometric reading at 555 nm.

Figure 3:
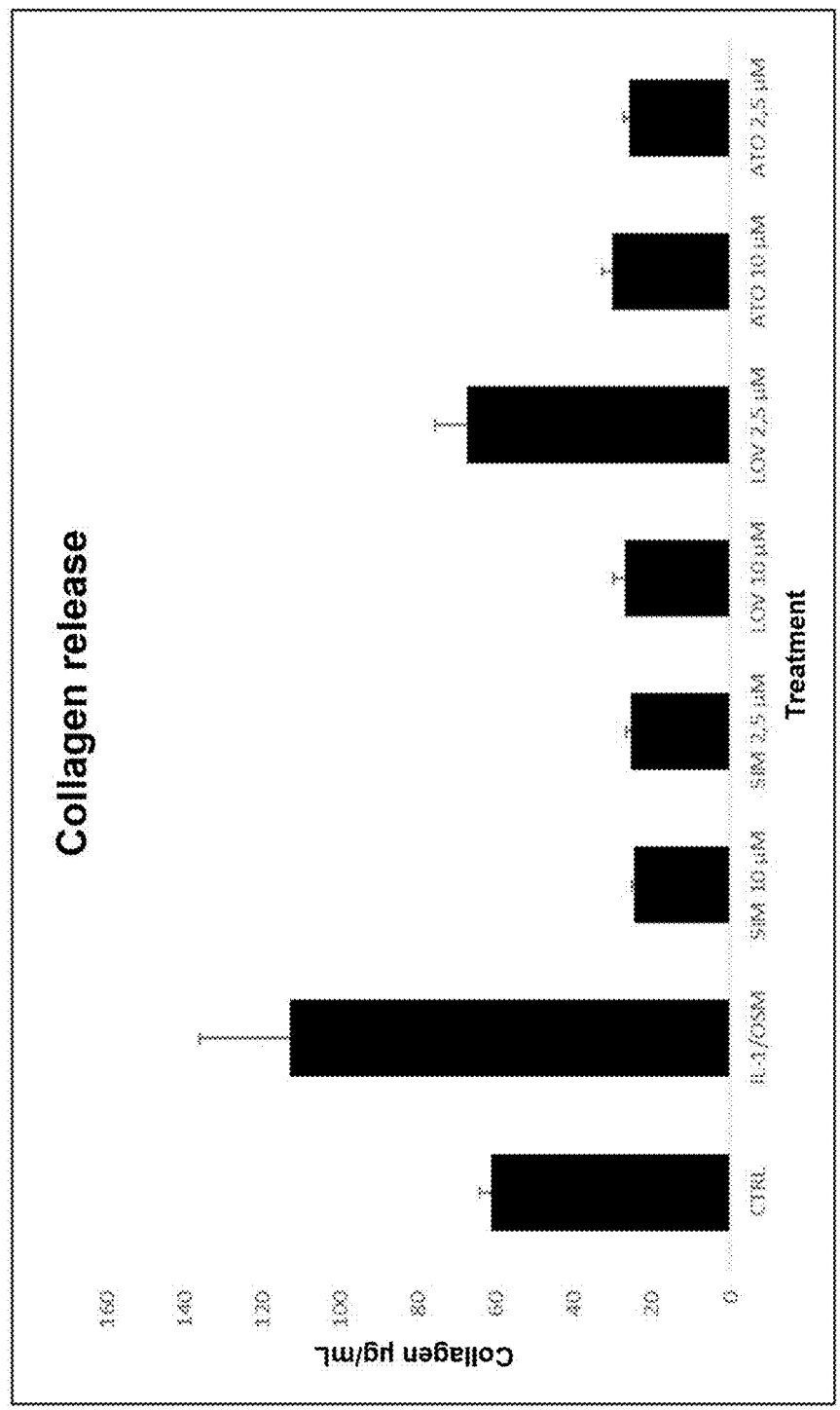
FIG. 3: comparison between the efficacy of the statins simvastatin (SIM), atorvastatin (ATO) and lovastatin (LOV).

As shown in FIG. 3, simvastatin is able to significantly reduce collagen release from biopsies treated with an inflammatory stimulus. The use of lovastatin, at the concentration of 10 μM, also led to a significant reduction in collagen release induced by treatment with IL-1β and OSM; when the lovastatin concentration was reduced (2.5 μM), an increase in collagen release is observed, with values comparable to those of the untreated control. Treatment of the biopsies with atorvastatin 10 and 2.5 μM led, as in the case of simvastatin, to a significant reduction in collagen release.

On the basis of the data obtained it can be concluded that all the statins used in the assay reduce collagen loss from bovine cartilage explants treated with an inflammatory stimulus; simvastatin and atorvastatin also seem to be more effective at lower concentrations (2.5 μM) than lovastatin.

BIBLIOGRAPHY

Akasaki et al 2009. *Mevastatin reduces cartilage degradation in rabbit experimental osteoarthritis through inhibition of synovial inflammation*. Osteoarthritis and Cartilage, 17, 235-243.

Baker et al., 2012. *Pravastatin suppresses matrix metalloproteinase expression and activity in human articular chondrocytes stimulated by interleukin-1b*. J Orthopaed Traumatol; 13:119-123.

Chang et al., 2014. *Anti-Inflammatory Effects of Hydrophilic and Lipophilic Statins with Hyaluronic Acid Against LPS-Induced Inflammation in Porcine Articular Chondrocytes*. J Orthop Res, 32, 557-65.

Clockaerts et al., 2012. *Statin use is associated with reduced incidence and progression of knee osteoarthritis in the Rotterdam study*. Ann Rheum Dis, 71:642-647.

Dinc et al., 2012. *An Assessment of the Chondroprotective Effects of Intra-Articular Application of Statin and Tetracycline on Early-Stage Experimental Osteoarthritis*. ISRN Orthopedics. doi: 10.5402/2012/182097.

Dombrecht et al., 2007. *Influence of simvastatin on the production of pro-inflammatory cytokines and nitric oxide by activated human chondrocytes*. Clinical and Experimental Rheumatology, 2007; 25: 534-539.

Dulak et al., 2005. *Anti-Angiogenic and Anti-Inflammatory Effects of Statins: Relevance to Anti-Cancer Therapy*. Curr Cancer Drug Targets. 5(8):579-94.

Goto et al, 2017. *A single intra-articular injection of fluvastatin-PLGA microspheres reduces cartilage degradation in rabbits with experimental osteoarthritis*. J Orthop Res., 35, 2465-2475.

Kadam et al., 2013. *Statin Use and Clinical Osteoarthritis in the General Population: A Longitudinal Study*. J Gen Intern Med 28(7):943-9.

Pathak et al., 2015. *Anti-inflammatory and chondroprotective effects of atorvastatin in a cartilage explant model of osteoarthritis*. Inflamm Res, 64, 161-9.

Yudoh et al., 2010. *Statin prevents chondrocyte aging and degeneration of articular cartilage in osteoarthritis (OA)*. Aging, 2, 990-8.

The invention claimed is:

1. A method of treating inflammation and degradation of osteoarthritic cartilage which comprises administering to a patient in need there of a composition,
   wherein the composition is in gel form and comprises a statin and a hyaluronic acid amide derivative selected from hexadecyl, octadecyl and dodecyl amide.

2. A method of treating post-traumatic osteoarthrosis, osteoarthrosis caused by physiological joint aging, and rheumatoid arthritis which comprises administering to a patient in need there of a composition,
   wherein the composition is in gel form and comprises a statin and a hyaluronic acid amide derivative selected from hexadecyl, octadecyl and dodecyl amide.

* * * * *